(12) United States Patent
Lou et al.

(10) Patent No.: US 9,993,215 B2
(45) Date of Patent: Jun. 12, 2018

(54) CT IMAGE CORRECTION

(71) Applicant: Shenyang Neusoft Medical Systems Co., Ltd., Shenyang (CN)

(72) Inventors: Shanshan Lou, Shenyang (CN); Changkun Liu, Shenyang (CN); Hongbo Wang, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 32 days.

(21) Appl. No.: 14/952,864

(22) Filed: Nov. 25, 2015

(65) Prior Publication Data

US 2016/0143604 A1 May 26, 2016

(30) Foreign Application Priority Data

Nov. 26, 2014 (CN) .......................... 2014 1 0695920

(51) Int. Cl.
*G06K 9/00* (2006.01)
*A61B 6/00* (2006.01)
(Continued)

(52) U.S. Cl.
CPC ............ *A61B 6/5205* (2013.01); *A61B 6/032* (2013.01); *A61B 6/5258* (2013.01); *G06T 7/337* (2017.01);
(Continued)

(58) Field of Classification Search
CPC .......................... G06T 2200/04; A61B 6/5205
See application file for complete search history.

(56) References Cited

U.S. PATENT DOCUMENTS 7,421,062 B2  9/2008  Okumura et al.
8,731,269 B2  5/2014  Nakanishi et al.
(Continued)

FOREIGN PATENT DOCUMENTS

CN    1689520 A     11/2005
CN    101398397 A    4/2009
(Continued)

OTHER PUBLICATIONS

Shouhua Luo, et al. Fitting Correction Method of Ring Artifacts for Reconstructing Cone-Beam CT Images. Transactions of Nanjing University of Aeronautics & Astronautics, 2010(1).
(Continued)

*Primary Examiner* — Oneal R Mistry
(74) *Attorney, Agent, or Firm* — Kilpatrick Townsend & Stockton LLP

(57) ABSTRACT

A method and system for CT image correction are provided. Contour data of a scanned subject can be obtained, and a shape image of the scanned subject can be reconstructed according to the contour data, wherein the contour data of the scanned subject can be obtained by scanning the scanned subject through a piece of visual equipment. Original CT projection data of the scanned subject can be obtained, and a CT image can be reconstructed according to the original CT projection data. For determining a supervision field image, image matching can be performed between the shape image and the CT image of the scanned subject. Supervision field projection data can be obtained, and the supervision field projection data can be used to correct the CT image.

14 Claims, 5 Drawing Sheets

(51) Int. Cl.
  *A61B 6/03* (2006.01)
  *G06T 11/00* (2006.01)
  *G06T 7/33* (2017.01)

(52) U.S. Cl.
  CPC ........ *G06T 11/005* (2013.01); *G06T 2200/04* (2013.01); *G06T 2207/10081* (2013.01); *G06T 2207/30204* (2013.01)

(56) References Cited

U.S. PATENT DOCUMENTS

| | | | |
|---|---|---|---|
| 8,737,711 | B2 | 5/2014 | Goto et al. |
| 9,418,451 | B2* | 8/2016 | Taguchi ................ G06T 11/003 |
| 2003/0130576 | A1* | 7/2003 | Seeley ..................... A61B 6/12 600/426 |
| 2007/0116171 | A1 | 5/2007 | Hsieh et al. |
| 2008/0073543 | A1 | 3/2008 | Vija et al. |
| 2011/0150312 | A1* | 6/2011 | Takanami ............... G06T 17/20 382/131 |
| 2011/0188723 | A1* | 8/2011 | Bruder .................. A61B 6/032 382/131 |
| 2013/0303898 | A1 | 11/2013 | Kinahan et al. |
| 2013/0322723 | A1* | 12/2013 | Akhbardeh ............ A61B 6/032 382/131 |
| 2015/0103969 | A1* | 4/2015 | Flohr ..................... A61B 6/032 378/4 |

FOREIGN PATENT DOCUMENTS

| | | |
|---|---|---|
| CN | 101574266 A | 11/2009 |
| CN | 101620191 A | 1/2010 |
| CN | 101862220 A | 10/2010 |
| CN | 103186883 A | 7/2013 |
| CN | 103366389 A | 10/2013 |
| CN | 103479379 A | 1/2014 |
| CN | 103714513 A | 4/2014 |
| CN | 103971387 A | 8/2014 |
| EP | 2662834 A1 | 11/2013 |
| EP | 2687261 A1 | 1/2014 |
| JP | 2011-172728 A | 9/2011 |
| JP | 2011-203160 A | 10/2011 |
| WO | 2014/123041 A1 | 8/2014 |
| WO | 2014/137325 A1 | 9/2014 |

OTHER PUBLICATIONS

Jianwei Gu, et al. The Review of Reasons and Correction Methods for Artifacts in ICT Images. Theory and Applications, 2005(3).

Lixin Zhang, Cradle Image Correction Method for CT Scout Scan Based on Image Registration, Journal of Tianjin University, vol. 39 No. 11, Nov. 2006, pp. 1375-1377.

Medhat M.OSman, Respiratory motion artifacts on PET emission images obtained using CT attenuation correction on PETCT, European Journal of Nuclear Medicine and Molecular Imaging, Jan. 21, 2003, vol. 30 No. 4, pp. 603-606.

\* cited by examiner

Sphere Markers

CT IMAGE CORRECTION

The present application claims the priority to Chinese Patent Applications No. 201410695920.X, filed with the Chinese State Intellectual Property Office on Nov. 26, 2014, which is incorporated herein by reference in its entirety.

BACKGROUND

The present disclosure is directed to Computed Tomography (CT), more particularly to CT image correction.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

CT (computed tomography) scan uses X-ray beams to scan a scanned subject and can see internal structures of the scanned subject without splitting the scanned subject, so CT scan is commonly used in inspections for various diseases. However, if the size of the scanned subject can be big (such as, a fat patient) or the position of the scanned subject is unreasonable during scanning, it may cause that the scanned subject deviates from the rotation centreline of the gantry of the CT device too much and a region of the scanned subject falls beyond the effective scan visual field of the CT scan system (i.e., the supervision field), which may lead to artefacts in the reconstructed CT image.

In order to correct the CT image's artefacts caused by the supervision field, a symmetrical mirror data extrapolation method or a water-mode-data-based extrapolation method is commonly used for estimating the contour of the scanned subject when the scanned subject is a human body which is supposed as an elliptical. However, if there are too many truncated regions in the supervision field or the shape can be complex, the deviation between the the estimated data and the actual situation will become too large, which makes the correction effect poor. Another method of combining data of the scanned subject generated by other imaging device (such as PET) can also be used for CT image correction, but this method may cause additional radiation damage to the scanned subject. Hence, providing a new CT image correction method is necessary in order to reduce the deviation of correction effect without causing additional radiation damage to the scanned subject.

Figure 1:
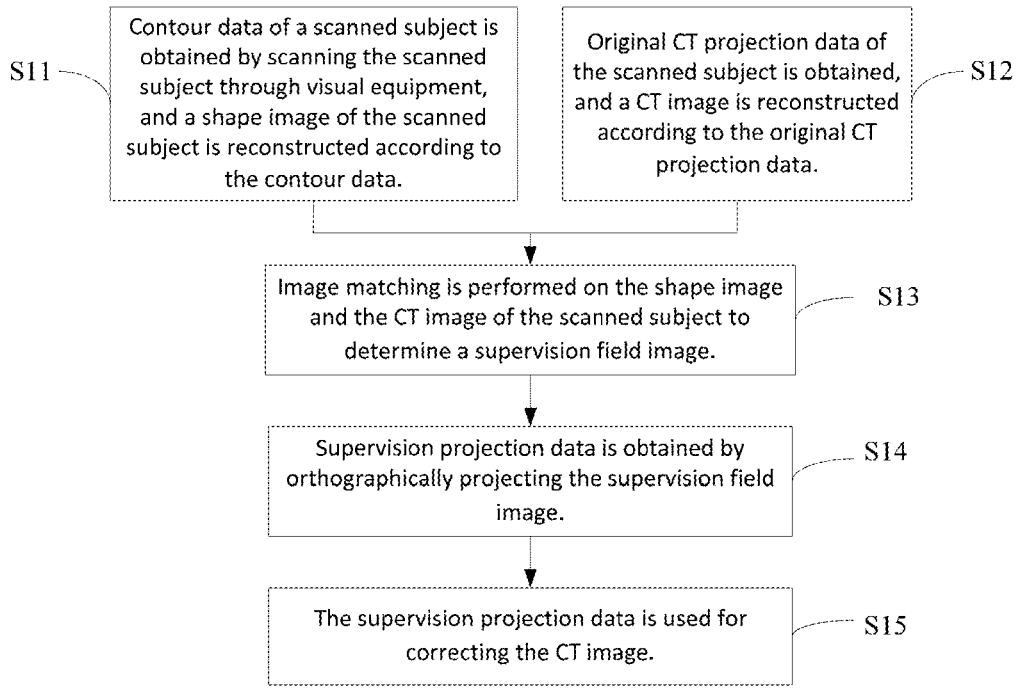
FIG. 1 is a flowchart illustrating a method for CT image correction according to an example of the present disclosure.

FIG. 1 is a flowchart illustrating a method for CT image correction according to an example of the present disclosure.

At block S11, contour data of a scanned subject is obtained by scanning the scanned subject through visual equipment, and a shape image of the scanned subject is reconstructed according to the contour data.

In this example, the visual equipment may be a 3D scanner, a thermal imaging device, or a camera. It should be understood that the visual equipment in the present disclosure is not limited to the abovementioned imaging devices; and any other visual equipment capable of obtaining the contour data of the scanned subject fall within the scope of the present disclosure. In order to improve the visual equipment's scanning speed for scanning the scanned subject, a plurality of visual equipment of the same type can be simultaneously employed or a plurality of different types of visual equipment can be simultaneously employed.

In an example, a 3D scanner is used for obtaining the contour data of the scanned subject. The 3D scanner uses a plurality of receivers to measure distances between a surface of an object under test and laser products by sending laser lights to the object under test based on optical imaging principles. The scan data obtained by the 3D scanner is then imported into a computer, and a 3D model of the scanned subject is converted by software. This 3D model can be used for determining the contour of the scanned subject. Existing 3D colour scanner can also restore the colour information of the scanned subject at the same time.

In another example, the thermal imaging device uses infrared detectors to receive infrared rays emitted from the scanned subject, and use optical principles and imaging devices to form an infrared thermography.

In practice, when the visual equipment is used for scanning the scanned subject located within the CT scan system, the visual equipment can be mounted on the gantry of the CT device. When visual equipment is mounted on the gantry of the CT device for scanning the scanned subject, the visual equipment can simultaneously rotate with the gantry. At this time, the visual equipment may be mounted on the inner side of rotation of the gantry of the CT device, and thus only one piece of visual equipment is required for collecting the contour data of the scanned subject. In another example, the visual equipment mounted on the gantry of the CT device does not need to simultaneously rotate with the gantry. At this time, multiple pieces of visual equipment may be required for collecting the contour data of the scanned subject. The multiple pieces of visual equipment may be placed at different locations of the gantry of the CT device in order to implement a full range of scanning of the scanned subject. For example, a plurality of 3D scanners may be used for covering the scan range.

In another example, the visual equipment is not mounted on the gantry of the CT device, wherein the visual equipment is a stand-alone device for scanning the contour of the scanned subject. For example, a large-scale visual equipment (such as, a stereoscopic 3D scanner) has a relatively large size and cannot be mounted on the gantry of the CT device, and can only be used as a stand-alone device for scanning the scanned subject. In other examples, a portable 3D scanner may be used for individually scanning the scanned subject.

It should be understood that, when the visual equipment is mounted on the gantry of the CT device for scanning the scanned subject, an appendage (such as, a tablelop) of the CT scan system may block the scanned subject. For this reason, the image obtained by the visual equipment may include an image of the appendage, and thus an overall contour of the scanned subject cannot be obtained. In this case, in order to obtain an overall contour of the scanned subject, block S11 may further include the following sub-blocks.

At block S111, the visual equipment is used to scan the scanned subject in order to obtain a scan data.

It should be understood that, the scan data obtained in this block may not only include the contour data of the scanned subject, and may also include the contour data of an appendages blocking the scanned subject At block S112, an original visual image of the scanned subject is reconstructed according to the scan data, wherein the reconstructed original visual image of the scanned subject may include an image of an appendage blocking the scanned subject.

At block S113, the image of the appendage is removed from the original visual image of the scanned subject in order to obtain the shape image of the scanned subject.

In an example, since there is an obvious difference between the CT attenuation value of the appendage and the CT attenuation value of the scanned subject's tissue, the image of the appendage can be divided from the CT image according to the CT attenuation value. After that, the image of the appendage is subtracted from the original visual image in order to obtain the shape image of the scanned subject.

In another example, since the size and the shape of the appendage are usually fixed, an image recognition technology can be used for subtracting the image of the appendage from the original visual image in order to obtain the shape image of the scanned subject.

At block S12, original CT projection data of the scanned subject is obtained, and a CT image is reconstructed according to the original CT projection data.

A CT scan is performed on the scanned subject, and X-ray is attenuated and reached the detector after passing the scanned subject. After that, a photoelectric signal is converted to an electric signal, and then the electric signal is transmitted to an image-building computer through a data management system. The attenuation value of X-ray after passing the scanned subject is the original CT projection data of the scanned subject.

The original CT projection data of the scanned subject is pre-processed, and then the CT image of the scanned subject is reconstructed according to the pre-processed original CT projection data by using FBP (Filtered Backprojection Algorithm) algorithm or iterative algorithm.

It should be understood that, in this example, the CT image can be the original CT image reconstructed according to the original CT projection data, or can be the CT image obtained by using existing supervision correction methods.

At block S13, image matching is performed on the shape image and the CT image of the scanned subject to determine a supervision field image.

Figure 2:
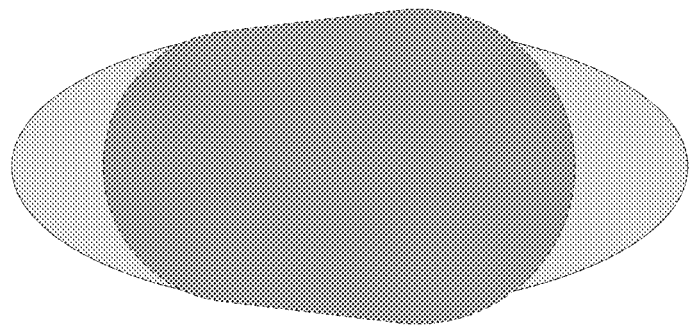
FIG. 2 is a diagram illustrating re-constructing shape image and CT image matching according to an example of the present disclosure.

The image matching is a process for overlapping the same region of the shape image and the CT image. The shape image is an overall image of the contour of the scanned subject, and the CT image is an image of the scanned subject located within the visual field of CT scan and usually may not include the image of the contour of the scanned subject located in the supervision field. However, there may be a great difference between the CT image obtained by using existing supervision correction methods and the actual image, and thus a region of the shape image is located beyond the region of the CT image after performing the image matching on the shape image and the CT image. As shown in FIG. 2, the solid line represents the peripheral contour of the shape image, and the dotted line represents the peripheral contour of the CT image, wherein the region of the shape image located beyond the dotted line represents the supervision field of the CT scan. The supervision field may lead to artefacts in the CT image, which can reduce the quality of the CT image. In order to reduce the CT image artefacts that resulted from the supervision field, CT image correction is performed.

It should be understood that, as mentioned at block S11, in an example, the contour data of the scanned subject can be obtained through a piece of visual equipment mounted on the gantry of the CT device; or in another example, the contour data of the scanned subject can be obtained through a piece of visual equipment not mounted on the gantry of the CT device. If the visual equipment is mounted on the gantry of the CT device, the view angle that the CT device and the visual equipment scan the scanned subject is fixed, and thus the shape image of the scanned subject obtained through the visual equipment mounted on the gantry of the CT device is consistent with the CT image obtained through CT scan in space. The shape image of the scanned subject obtained through the visual equipment not mounted on the gantry of the CT device is not consistent with the CT image obtained through CT scan in space and the position relationship between them is not fixed, and thus the image matching methods corresponding to these two cases are different 1. In a first case, the contour data of the scanned subject is obtained through the visual equipment mounted on the gantry of the CT device.

Since the CT image obtained through CT scan is consistent with the shape image of the scanned subject obtained through the visual equipment in space, a relative position relationship between the CT image and the shape image can be easily obtained according to their output images. The image matching is then performed on the shape image and the CT image according to the relative position relationship in order to determine the supervision field image.

2. In a second case, the contour data of the scanned subject is obtained through the visual equipment not mounted on the gantry of the CT device.

In this case, the relative position relationship between the shape image of the scanned subject obtained through the visual equipment and the CT image obtained through CT scan is not fixed. When performing the image matching, an image matching algorithm is performed for automatically matching the CT image and the shape image obtained through the visual equipment, or the image matching position is assigned by users through Human Machine interactions.

Under the condition that the contour data of the scanned subject is obtained through the visual equipment not mounted on the gantry of the CT device, further description is detailed below. If an image matching is directly employed, the accuracy of the image matching is lower, and the computational complexity of the image matching algorithm is higher. In order to improve the accuracy of the image matching and to reduce the computational complexity, a positioning assisting device can be placed on the scanned subject in advance, wherein the positioning assisting device is used for assisting the image matching of the shape image and the CT image. No matter which scanning methods are used for scanning the scanned subject, the relative position of the positioning assisting device in each scan image is changed. When the positioning assisting device in different images is matched, the image matching is also completed. That is, through the matching of the positioning assisting device in different images, the image matching is completed. It should be noted that, the matching of the positioning assisting device in different images can be implemented by a characteristic matching of one or multiple characteristics of the positioning assisting device.

In an example, the positioning assisting device is fixed on the scanned subject for easy installation. The position that the positioning assisting device placed on the scanned subject should be easy to be scanned by the visual equipment and the positioning assisting device cannot block the visual equipment from scanning the scanned subject, so that the shape image of the scanned subject output through the visual equipment won't be affected.

In order to facilitate recognition of the positioning assisting device in the CT image, the CT attenuation value of the positioning assisting device should be different from the CT attenuation value of the scanned subject and cannot lead to artefacts in the CT image. In an example, the positioning assisting device manufactured by substances with smaller X-ray attenuation coefficients (such as, plastic materials) can be selected for making the CT attenuation value of the positioning assisting device satisfying the abovementioned requirements. Metal materials, such as gold, silver, and iron usually lead to metal artefacts in the CT image, and thus metal materials usually are not selected for manufacturing the positioning assisting device.

In another example, when the visual equipment is a 3D scanner, the exterior shape of the positioning assisting device should not be confused with the scanned subject for easily screening out the positioning assisting device from the shape image. When the visual equipment is a thermal imager, the temperature property of the positioning assisting device should be different from the temperature property of the scanned subject.

The positioning assisting device can be placed within the visual field of CT image for easily searching the positioning assisting device in the CT image.

The positioning assisting device may include a plurality of markers for improving the accuracy of the image matching, wherein size, shape, material, and color of each marker can be the same or different.

In order to facilitate recognition of the markers of the positioning assisting device in the shape image and the CT image, these markers can be separately placed on the body of the scanned subject, rather than overlapped and stacked. In an example, the shape of the markers can be sphere or cube, and etc. for easy recognition.

Figure 3:
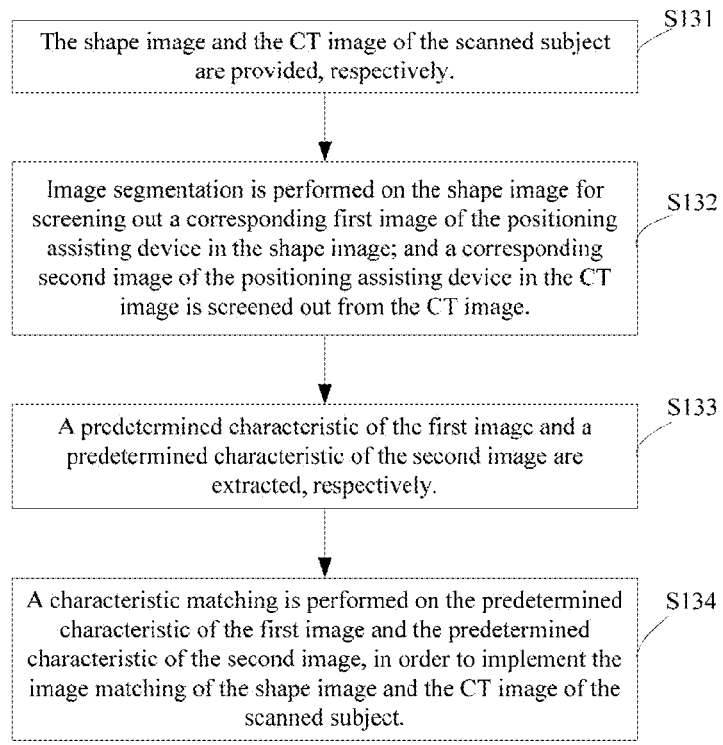
FIG. 3 is a flowchart illustrating a method for image matching by using a positioning assisting device according to an example of the present disclosure.

FIG. 3 is a flowchart illustrating a method for image matching by using a positioning assisting device according to an example of the present disclosure. The method includes the following blocks.

At block S131, the shape image and the CT image of the scanned subject are provided, respectively.

At block S132, image segmentation is performed on the shape image for screening out a corresponding first image of the positioning assisting device in the shape image; and a corresponding second image of the positioning assisting device in the CT image is screened out from the CT image.

The difference between the positioning assisting device and the scanned subject (such as different colors, different shapes, or different temperature properties) can be used for performing the image segmentation on the shape image in order to screen out a corresponding first image of the positioning assisting device in the shape image. The different CT attenuation values are used for screening out a corresponding second image of the positioning assisting device from the CT image At block S133, a predetermined characteristic of the first image and a predetermined characteristic of the second image are extracted, respectively.

It should be noted that, the predetermined characteristic may be one or any number of combinations of an edge, a contour, a center, and a corner of a corresponding image of the positioning assisting device, wherein the predetermined characteristic extracted from the first image is the same as the predetermined characteristic extracted from the second image.

At block S134, a characteristic matching is performed on the predetermined characteristic of the first image and the predetermined characteristic of the second image, in order to implement the image matching of the shape image and the CT image of the scanned subject.

A characteristic matching method may be employed for performing the characteristic matching on the predetermined characteristic in the shape image and the predetermined characteristic in the CT image. After the predetermined characteristics are matched, the image matching of the shape image and the CT image of the scanned subject is completed.

In an example of the present disclosure, the block of performing a characteristic matching on the predetermined characteristic of the first image and the predetermined characteristic of the second image may further include the following blocks.

At block S134a, the predetermined characteristic of the first image is set to form a first predetermined pattern, and the predetermined characteristic of the second image is set to form a second predetermined pattern.

At block S134b, a rotation-and-translation matrix of converting the first predetermined pattern to the second predetermined pattern is calculated.

At block S134c, a spatial transformation is performed on the shape image based on the rotation-and-translation matrix, in order to implement the characteristic matching of the predetermined characteristic of the shape image and the predetermined characteristic of the CT image.

In order to more clearly understand the process for using the positioning assisting device to implement the image matching of the shape image and the CT image in this example, a specific scenario below is used for detailed description.

Figure 4:
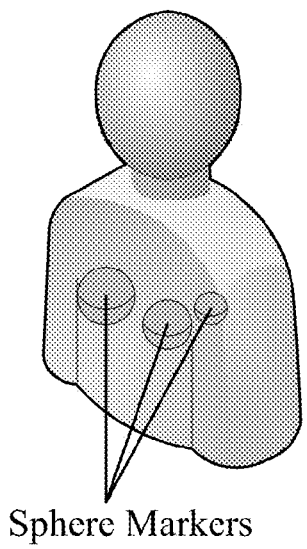
FIG. 4 is a diagram showing a placement of the positioning assisting device on the scanned subject according to an example of the present disclosure.

As shown in FIG. 4, in this scenario, the positioning assisting device includes three sphere markers. Before scanning, the three sphere markers are placed on the scanned subject. The three sphere markers are separately placed, rather than overlapped and stacked, for easy recognition. In this scenario, the position relationship of the three sphere markers placed on the scanned subject is a triangle, and the positions of the three sphere markers are located within the effective visual field of the CT scan.

Figure 5:
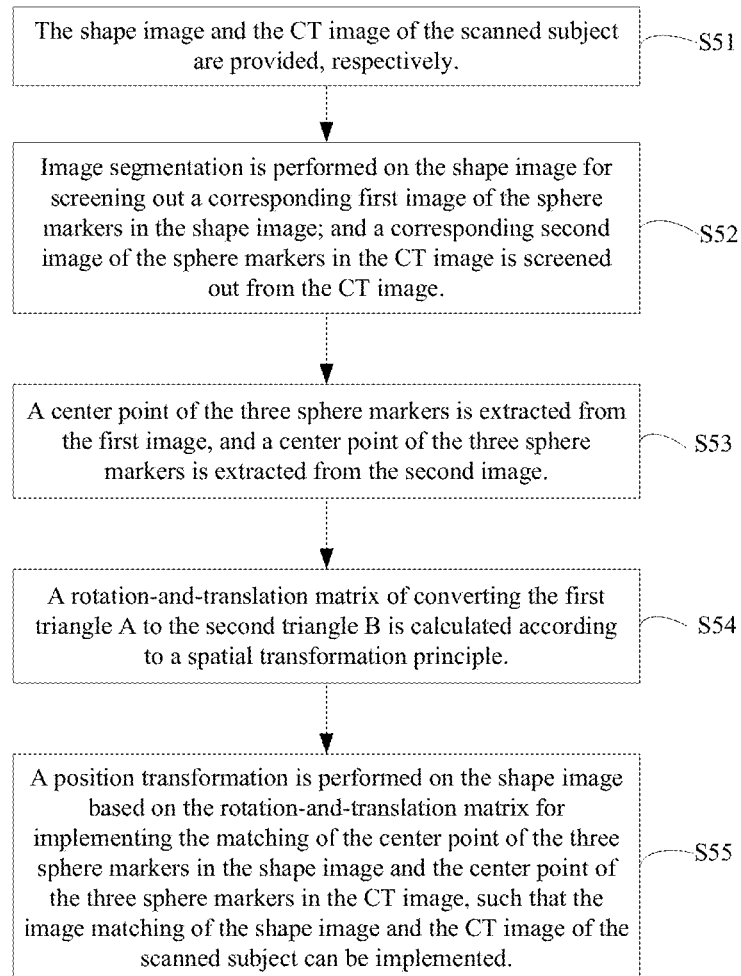
FIG. 5 is a flowchart illustrating the procedures of a method for image matching by using a positioning assisting device according to another example of the present disclosure.

FIG. 5 is a flowchart illustrating the procedures of a method for image matching by using a positioning assisting device (the three sphere markers) according to an example of the present disclosure. FIG. 5 may include the following blocks.

At block S51, the shape image and the CT image of the scanned subject are provided, respectively.

Since the three sphere markers are placed on the scanned subject before CT scan, the shape image generated by the visual equipment includes the image of the sphere markers. Similarly, the CT image also includes the image of the sphere markers.

At block S52, image segmentation is performed on the shape image for screening out a corresponding first image of the sphere markers in the shape image; and a corresponding second image of the sphere markers in the CT image is screened out from the CT image.

At block S53, a center point of the three sphere markers is extracted from the first image, and a center point of the three sphere markers is extracted from the second image.

At this time, the pattern formed by the center point of the three sphere markers being extracted from the first image is defined as a first triangle A, and the pattern formed by the center point of the three sphere markers being extracted from the second image is defined as a second triangle B.

At block S54, a rotation-and-translation matrix of converting the first triangle A to the second triangle B is calculated according to a spatial transformation principle.

At block S55, a position transformation is performed on the shape image based on the rotation-and-translation matrix for implementing the matching of the center point of the three sphere markers in the shape image and the center point of the three sphere markers in the CT image, such that the image matching of the shape image and the CT image of the scanned subject can be implemented.

It should be understood that, the number of the markers of the positioning assisting device is not limited to three only, and can be other numbers, such as, two, five, and six, etc. Additionally, the markers can be of other shapes, such as a cube.

At block S14, supervision projection data is obtained by orthographically projecting the supervision field image.

In an example, block S14 may be implemented by the following sub-blocks.

At block S14a, an initial CT value is filled in the supervision field.

Specifically, the CT value that is similar to the CT value of the scanned subject's tissue can be used for filling the initial CT value in the supervision field, and the material having the initial CT value that is similar to the CT value of the scanned subject's tissue may be water. In another example, except that the similar CT value can be used for filling in the supervision field, the CT value of the symmetric region of the scanned subject can be used for filling in the supervision field if the symmetric region of the scanned subject does not exceed the visual field. In another example, the initial CT value within the supervision field can be estimated by adopting a maximum likelihood estimation method.

At block S14b, a CT attenuation value is generated by using a simulated X-ray to irradiate the filled supervision field, in order to obtain the supervision projection data.

At block S15, the supervision projection data is used for correcting the CT image.

Specifically, the supervision projection data and the original projection data of the CT scan are combined to perform interpolation smoothing in the transition area for avoiding strip artefacts. The corrected CT projection data is obtained, and is then used for reconstructing the corrected CT image.

The above is an exemplary illustration of a CT image correction method in accordance with the present disclosure. In this CT image correction method, the overall shape image of the scanned subject can be obtained through the visual equipment. Since the visual equipment does not cause additional X-ray radiation damage to the scanned subject, a correction method in accordance with the present disclosure can effectively reduce the damage to the scanned subject, compared to existing technology using X-ray radiation means for obtaining the overall shape image of the scanned subject. Even if the contour of the scanned subject is very complex, the visual equipment can also accurately obtain the contour of the scanned subject. Hence, the deviation between the obtained contour of the scanned subject and the actual contour can be reduced through the visual equipment, which improves the correction effect of using the interpolation method to correct the supervision field image.

Figure 6:
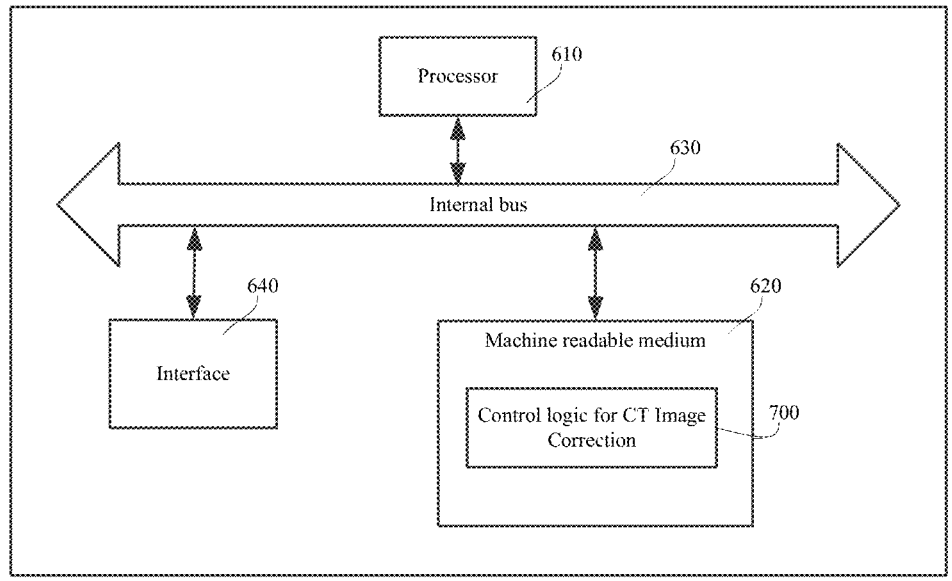
FIG. 6 is a hardware architecture diagram of a device for CT image correction according to an example of the present disclosure.

In accordance with the abovementioned CT image correction method, a device for CT image correction is provided in the present disclosure. Please refer to FIG. 6. In an example, the device may include a processor such as a CPU 610 and storage medium 620 that can be configured to store machine-readable instructions, wherein the processor 610 is connected to the machine readable storage medium 620 through an internal bus 630. In other possible implementations, the device may include an interface 640 for communicating with other devices or components.

In different examples, the storage medium 620 may include Random Access Memory (RAM), volatile memory, non-volatile memory, flash memory, storage drives (such as, hard drive), solid state drive, any type of storage disks (such as, CD-ROM, DVD, etc.), or similar storage medium, or a combination thereof.

Figure 7:
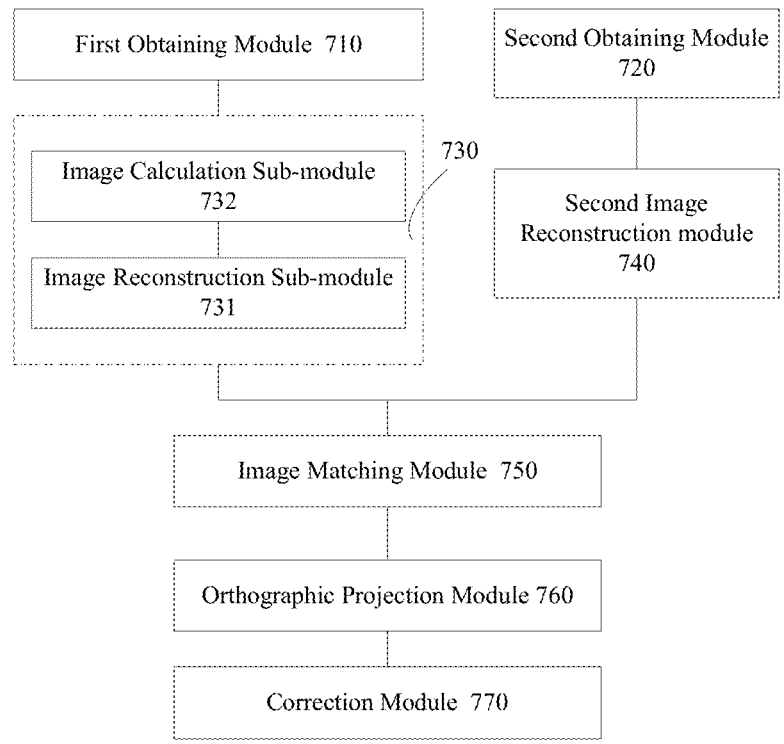
FIG. 7 is a block diagram of the control logic for CT image correction according to an example of the present disclosure.

In an example, storage medium 620 can be configured to store machine readable instructions corresponding to control logic 700 for CT image correction. As shown in FIG. 7, a block diagram of the control logic 700 may further include a first obtaining module 710, a second obtaining module 720, a first image reconstruction module 730, a second image reconstruction module 740, an image matching module 750, an orthographic projection module 760, and a correction module 770.

The first obtaining module 710 can be configured to obtain contour data of a scanned subject, wherein the contour data of the scanned subject is obtained by scanning the scanned subject through a piece of visual equipment.

The second obtaining module 720 can be configured to obtain original CT projection data of the scanned subject.

The first image reconstruction module 730 can be configured to reconstruct a shape image of the scanned subject according to the contour data.

The second image reconstruction module 740 can be configured to reconstruct a CT image according to the original CT projection data.

The image matching module 750 can be configured to perform an image matching on the shape image and the CT image of the scanned subject in order to determine a supervision field image.

The orthographic projection module 760 can be configured to obtain a supervision projection data by orthographically projecting the supervision field image.

The correction module 770 can be configured to use the supervision projection data to correct the CT image.

Through the control logic 700 for CT image correction, both the radiation damage to the scanned subject and the correction deviation can be reduced.

In order to improve the accuracy of the image matching, a positioning assisting device can be placed on the scanned subject, wherein the positioning assisting device is used for assisting the image matching of the shape image and the CT image.

In an example, the visual equipment can be mounted on the rotating gantry of the CT device. In order to obtain the overall shape image of the scanned subject, the first obtaining module 710 may include sub-modules for obtaining scan data by scanning the scanned subject through the visual equipment.

The first image reconstruction module 730 may further include an image reconstruction sub-module 731 and an image calculation sub-module 732.

The image reconstruction sub-module 731 can be configured to reconstruct an original visual image according to the scan data, wherein the reconstructed original visual image can include an image of an appendage blocking the scanned subject.

The image calculation sub-module 732 can be configured to remove the image of the appendage from the original visual image in order to obtain the shape image of the scanned subject.

Figure 8:
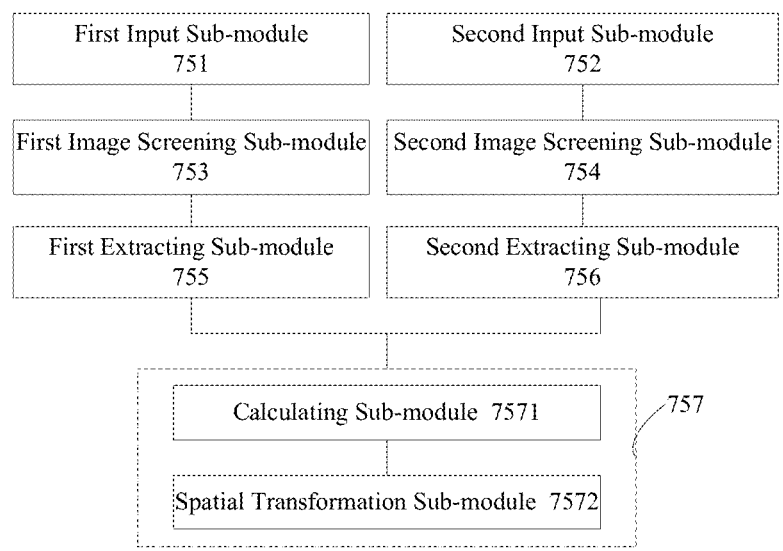
FIG. 8 is a sub-block diagram of an image matching module according to an example of the present disclosure.

In another example, the visual equipment can be not mounted on the rotating gantry of the CT device, wherein the visual equipment is a stand-alone device for scanning the scanned subject. As shown in FIG. 8, in order to implement the accuracy of the image matching of the shape image and the CT image, the image matching module 750 may further include a first input sub-module 751, a second input sub-module 752, a first image screening sub-module 753, a second image screening sub-module 754, a first extracting sub-module 755, a second extracting sub-module 756, and a characteristic matching sub-module 757.

The first input sub-module 751 can be configured to provide the shape image.

The second input sub-module 752 can be configured to provide the CT image.

The first image screening sub-module 753 can be configured to perform image segmentation on the shape image for screening out a corresponding first image of the positioning assisting device in the shape image.

The second image screening sub-module 754 can be configured to screen out a corresponding second image of the positioning assisting device from the CT image.

The first extracting sub-module 755 can be configured to extract a predetermined characteristic of the first image, wherein the predetermined characteristic can include one or any number of combinations of an edge, a contour, a center, and a corner of a corresponding image of the positioning assisting device.

The second extracting sub-module 756 can be configured to extract a predetermined characteristic of the second image.

The characteristic matching sub-module 757 can be configured to perform characteristic matching on a predetermined characteristic of the first image and a predetermined characteristic of the second image, in order to implement the image matching of the shape image and the CT image of the scanned subject.

The predetermined characteristic of the first image can be set to form a first predetermined pattern, and the predetermined characteristic of the second image can be set to form a second predetermined pattern. The characteristic matching sub-module 757 may further include a calculating sub-module 7571 and a spatial transformation sub-module 7572.

The calculating sub-module 7571 can be configured to calculate a rotation-and-translation matrix of converting the first predetermined pattern to the second predetermined pattern.

The spatial transformation sub-module 7572 can be configured to perform a spatial transformation on the shape image based on the rotation-and-translation matrix, in order to implement the characteristic matching of the predetermined characteristic of the shape image and the predetermined characteristic of the CT image.

The example below is implemented with software, which describes how the device for CT image correction runs the control logic 700. In this example, the control logic 700 of the present disclosure should be understood as machine readable instructions stored in the storage medium 620. When the processor 610 of the device for CT image correction executes the control logic 700, the processor 610 executes machine readable instructions corresponding to the control logic 700 stored in the storage medium 620 to:

obtain contour data of a scanned subject, and reconstruct a shape image of the scanned subject according to the contour data, wherein the contour data of the scanned subject is obtained by scanning the scanned subject through a piece of visual equipment;

obtain original CT projection data of the scanned subject, and reconstruct a CT image according to the original CT projection data;

perform image matching on the shape image and the CT image of the scanned subject in order to determine a supervision field image; and obtain supervision projection data, and use the supervision projection data to correct the CT image.

When the visual equipment is mounted on the rotating gantry of the CT device, the processor 610 executing machine readable instructions corresponding to the control logic 700 for CT image correction to reconstruct a shape image of the scanned subject according to the contour data causes the processor 610 to:

use the visual equipment to scan the scanned subject in order to obtain a scan data;

reconstruct an original visual image of the scanned subject according to the scan data, wherein the reconstructed original visual image of the scanned subject includes an image of the appendage blocking the scanned subject; and remove the image of the appendage from the original visual image of the scanned subject in order to obtain the shape image of the scanned subject.

When the visual equipment is mounted on the rotating gantry of the CT device, the processor 610 executing machine readable instructions corresponding to the control logic 700 for CT image correction to perform an image matching on the shape image and the CT image of the scanned subject causes the processor 610 to:

obtain a relative position relationship between the shape image and the CT image according to a consistency between the shape image and the CT image of the scanned subject in space; and perform the image matching on the shape image and the CT image of the scanned subject according to the relative position relationship.

In an example, a positioning assisting device is placed on the scanned subject, wherein the positioning assisting device is used for assisting the image matching of the shape image and the CT image When the visual equipment is not mounted on the rotating gantry of the CT device, the processor 610 executing machine readable instructions corresponding to the control logic 700 for CT image correction to perform an image matching on the shape image and the CT image of the scanned subject causes the processor 610 to:

provide the shape image and the CT image of the scanned subject, respectively;

perform an image segmentation on the shape image for screening out a corresponding first image of the positioning assisting device in the shape image;

screen out, from the CT image, a corresponding second image of the positioning assisting device in the CT image;

extract a predetermined characteristic of the first image and a predetermined characteristic of the second image, respectively;

perform a characteristic matching on the predetermined characteristic of the first image and the predetermined characteristic of the second image, in order to implement the image matching of the shape image and the CT image of the scanned subject.

In an example, the processor 610 executing machine readable instructions of the control logic 700 for CT image correction to perform a characteristic matching on the predetermined characteristic of the first image and the predetermined characteristic of the second image causes the processor 610 to:

set the predetermined characteristic of the first image to form a first predetermined pattern, and set the predetermined characteristic of the second image to form a second predetermined pattern;

calculate a rotation-and-translation matrix of converting the first predetermined pattern to the second predetermined pattern; and perform a spatial transformation on the shape image based on the rotation-and-translation matrix, in order to implement the characteristic matching of the predetermined characteristic of the shape image and the predetermined characteristic of the CT image.

In an example, the predetermined characteristic includes one or any number of combinations of an edge, a contour, a center, and a corner of a corresponding image of the positioning assisting device.

In an example, the positioning assisting device comprises a plurality of markers.

In an example, the processor 610 executing machine readable instructions corresponding to the control logic 700 for CT image correction to obtain a supervision projection data, and use the supervision projection data to correct the CT image causes the processor 610 to:

obtain the supervision projection data by orthographically projecting the supervision field image; and use the supervision projection data to correct the CT image.

In an example, the processor 610 executing machine readable instructions of the control logic 700 for CT image correction to obtain the supervision projection data by orthographically projecting the supervision field image causes the processor 610 to:

fill an initial CT value in the supervision field; and generate a CT attenuation value by using a simulated X-ray to irradiate the filled supervision field, in order to obtain the supervision projection data.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' can be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for CT image correction, the method comprising:
    obtaining contour data of a scanned subject;
    reconstructing a shape image of the scanned subject according to the contour data, wherein the contour data of the scanned subject is obtained by scanning the scanned subject through visual equipment;
    obtaining original CT projection data of the scanned subject; and
    reconstructing a CT image according to the original CT projection data;
    determining an image of a supervision field by performing image matching between the shape image and the CT image of the scanned subject;
    obtaining supervision field projection data, and using the supervision projection data to correct the CT image;
    placing a positioning assisting device on the scanned subject, wherein the positioning assisting device assists the image matching of the shape image and the CT image;
    wherein performing an image matching between the shape image and the CT image of the scanned subject when the visual equipment is not mounted on the gantry of the CT device comprises:
    providing the shape image and the CT image of the scanned subject, respectively;
    performing image segmentation on the shape image for screening out a corresponding first image of the positioning assisting device in the shape image;
    screening out, from the CT image, a corresponding second image of the positioning assisting device in the CT image;
    extracting a predetermined characteristic of the first image and a predetermined characteristic of the second image, respectively;
    implementing the image matching of the shape image and the CT image of the scanned subject by performing a characteristic matching on the predetermined characteristic of the first image and the predetermined characteristic of the second image;
    wherein performing a characteristic matching on the predetermined characteristic of the first image and the predetermined characteristic of the second image comprises:
    setting the predetermined characteristic of the first image to form a first predetermined pattern, and setting the predetermined characteristic of the second image to form a second predetermined pattern;
    calculating a rotation-and-translation matrix according to the first predetermined pattern and the second predetermined pattern, wherein the rotation-and-translation matrix is used to convert the first predetermined pattern to the second predetermined pattern; and
    implementing the characteristic matching of the predetermined characteristic of the shape image and the predetermined characteristic of the CT image by performing a spatial transformation on the shape image based on the rotation-and-translation matrix.

2. The method of claim 1, wherein when the visual equipment is mounted on a gantry of a CT device, said reconstructing the shape image of the scanned subject according to the contour data comprises:
    obtaining scan data by scanning the scanned subject with the visual equipment;
    reconstructing an original visual image of the scanned subject according to the scan data, wherein the reconstructed original visual image of the scanned subject comprises an image of an appendage blocking the scanned subject; and
    obtaining the shape image of the scanned subject by removing the image of the appendage from the original visual image of the scanned subject.

3. The method of claim 1, wherein when the visual equipment is mounted on the gantry of the CT device, said performing the image matching on the shape image and the CT image of the scanned subject comprises:
    obtaining a relative position relationship between the shape image and the CT image according to a consistency between the shape image and the CT image of the scanned subject in space; and
    performing the image matching on the shape image and the CT image of the scanned subject according to the relative position relationship.

4. The method of claim 1, wherein the predetermined characteristic comprises one or any number of combinations of an edge, a contour, a center, and a corner of a corresponding image of the positioning assisting device.

5. The method of claim 1, said obtaining the supervision field projection data, and using the supervision projection data to correct the CT image comprises:
    obtaining the supervision field projection data by orthographically projecting the supervision field image; and
    using the supervision projection data to correct the CT image.

6. The method of claim 5, wherein said obtaining the supervision projection data by orthographically projecting the supervision field image comprises:
    filling an initial CT value in the supervision field; and
    obtain the supervision projection data by generating a CT attenuation value by using a simulated X-ray to irradiate the filled supervision field.

7. The method of claim 1, wherein the positioning assisting device comprises a plurality of markers.

8. A device for CT image correction, the device comprising:
    a processor configured to execute machine-readable instructions corresponding to a control logic for CT image correction stored on a storage medium, wherein the machine-readable instructions, when executed, cause the processor to:
    obtain contour data of a scanned subject, and reconstruct a shape image of the scanned subject according to the contour data, wherein the contour data of the scanned subject is obtained by scanning the scanned subject through a piece of visual equipment;
    obtain original CT projection data of the scanned subject, and reconstruct a CT image according to the original CT projection data;
    determine an image of a supervision field by performing image matching between the shape image and the CT image of the scanned subject; and
    obtain a supervision projection data, and use the supervision projection data to correct the CT image;
    the device further comprises a positioning assisting device, placed on the scanned subject, wherein the positioning assisting device is used to assist the image matching of the shape image and the CT image;
    the machine readable instructions cause the processor to:
    provide the shape image and the CT image of the scanned subject, respectively;

perform image segmentation on the shape image for screening out a corresponding first image of the positioning assisting device in the shape image;

screen out, from the CT image, a corresponding second image of the positioning assisting device in the CT image;

extract a predetermined characteristic of the first image and a predetermined characteristic of the second image, respectively;

implement the image matching of the shape image and the CT image of the scanned subject by performing characteristic matching on the predetermined characteristic of the first image and the predetermined characteristic of the second image;

the machine readable instructions cause the processor to:

set the predetermined characteristic of the first image to form a first predetermined pattern, and set the predetermined characteristic of the second image to form a second predetermined pattern;

calculate a rotation-and-translation matrix according to the first predetermined pattern and the second predetermined pattern, wherein the rotation-and-translation matrix is used to convert the first predetermined pattern to the second predetermined pattern; and implement the characteristic matching of the predetermined characteristic of the shape image and the predetermined characteristic of the CT image by performing a spatial transformation on the shape image based on the rotation-and-translation matrix.

9. The device according to claim 8, wherein said machine readable instructions further cause the processor to:

obtain scan data by scanning the scanned subject using the visual equipment;

reconstruct an original visual image of the scanned subject according to the scan data, wherein the reconstructed original visual image of the scanned subject comprises an image of the appendage blocking the scanned subject; and obtain the shape image of the scanned subject by removing the image of the appendage from the original visual image of the scanned subject.

10. The device according to claim 8, wherein said machine readable instructions further cause the processor to:

obtain a relative position relationship between the shape image and the CT image according to a consistency between the shape image and the CT image of the scanned subject in space; and perform the image matching on the shape image and the CT image of the scanned subject according to the relative position relationship.

11. The device according to claim 8, wherein the predetermined characteristic comprises one or any number of combinations of an edge, a contour, a center, and a corner of a corresponding image of the positioning assisting device.

12. The device according to claim 8, wherein said machine readable instructions further cause the processor to:

obtain the supervision field projection data by orthographically projecting the supervision field image; and use the supervision field projection data to correct the CT image.

13. The device according to claim 12, wherein said machine readable instructions further cause the processor to:

fill an initial CT value in the supervision field; and obtain the supervision projection data by generating a CT attenuation value by using a simulated X-ray to irradiate the filled supervision field.

14. The device according to claim 8, wherein the positioning assisting device comprises a plurality of markers.

* * * * *